(12) United States Patent
Lee et al.

(10) Patent No.: US 10,815,533 B2
(45) Date of Patent: Oct. 27, 2020

(54) BIOMARKER FOR DIAGNOSING ANTICANCER DRUG RESISTANCE OF GASTRIC CANCER AND USE THEREOF

(71) Applicant: SAMSUNG LIFE PUBLIC WELFARE FOUNDATION, Seoul (KR)

(72) Inventors: Jeeyun Lee, Seoul (KR); Kyoung Mee Kim, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 0 days.

(21) Appl. No.: 16/166,688

(22) Filed: Oct. 22, 2018

(65) Prior Publication Data

US 2019/0127806 A1    May 2, 2019

(30) Foreign Application Priority Data

Oct. 31, 2017   (KR) .................. 10-2017-0143200

(51) Int. Cl.

| | | |
|---|---|---|
| *C12Q 1/68* | (2018.01) | |
| *C12Q 1/6886* | (2018.01) | |
| *C12Q 1/6881* | (2018.01) | |
| *G16H 50/20* | (2018.01) | |

(52) U.S. Cl.
CPC ......... *C12Q 1/6886* (2013.01); *C12Q 1/6881* (2013.01); *G16H 50/20* (2018.01); *C12Q 2600/106* (2013.01); *C12Q 2600/112* (2013.01); *C12Q 2600/118* (2013.01); *C12Q 2600/156* (2013.01)

(58) Field of Classification Search
None
See application file for complete search history.

(56) References Cited

PUBLICATIONS

Kim, S. Y., et al.; "Acquired resistance to LY2874455 in FGFR2-amplified gastric cancer through an emergence of novel FGFR2-ACSL5 fusion", Oncotarget, 2017, vol. 8, (No. 9), pp. 15014-15022.

*Primary Examiner* — Katherine D Salmon
(74) *Attorney, Agent, or Firm* — Harness, Dickey & Pierce, P.L.C.

(57) ABSTRACT

The present invention relates to a biomarker composition for diagnosing anticancer drug resistance of gastric cancer, including an FGFR2-ACSL5 fusion gene or a protein that the fusion gene encodes, a composition and a kit for diagnosing anticancer drug resistance of gastric cancer, including a preparation which detects an mRNA or protein of the fusion gene, and a method for diagnosing anticancer drug resistance of gastric cancer by using the biomarker. It is possible to diagnose in advance whether resistance to the drug will be exhibited during the treatment with the FGFR inhibitor by detecting an mRNA of the FGFR2-ACSL5 fusion gene according to the present invention or a protein which the gene encodes in a tissue derived from the patient with gastric cancer, so that the treatment efficiency can be enhanced by applying a more appropriate treatment to the patient.

3 Claims, 7 Drawing Sheets
Specification includes a Sequence Listing.

BIOMARKER FOR DIAGNOSING ANTICANCER DRUG RESISTANCE OF GASTRIC CANCER AND USE THEREOF

CROSS-REFERENCE TO RELATED APPLICATION

This application claims priority to and the benefit of Korean Patent Application No. 10-2017-0143200, filed on Oct. 31, 2017, the disclosure of which is incorporated herein by reference in its entirety.

FIELD

The present invention relates to a biomarker for diagnosing anticancer drug resistance of gastric cancer and a use thereof, and more particularly, to a biomarker composition for diagnosing anticancer drug resistance of gastric cancer, including a FGFR2-ACSL5 fusion gene or a protein that the fusion gene encodes, a composition and a kit for diagnosing anticancer drug resistance of gastric cancer, including a preparation which detects an mRNA or protein of the fusion gene, and a method for diagnosing anticancer drug resistance of gastric cancer by using the biomarker.

BACKGROUND

FGFR1-4, which is a fibroblast growth factor (FGF) receptor, belongs to the receptor-tyrosine kinase family, and when FGF, which is a ligand, binds to the receptor, a FGFR complex is formed while a FGF dimer is formed, so that the kinase activation and auto-phosphorylation of multiple tyrosine residues in the cytoplasmic domain of the receptor are induced. As a result, the activation of sub phosphoinositide 3-kinase (PI3K)-AKT and mitogen-activated protein kinase (MAPK)-extracellular signal regulated kinase (ERK) signaling pathways occurs. The frequency at which FGFR2 amplification is observed in gastric cancer (GC) has been reported to be 2% to 9%, and the FGFR2 amplification and the amplification of MET and HER2 are known to be mutually exclusive. For example, as a result of a study of screening whether FGFR2 is amplified in samples of 764 patients with gastric cancer (408 Caucasian patients and 356 Korean patients), it was reported that FGFR2 was slightly more amplified in the Caucasian patients (7.4%, 30/408) than in the Korean patients (4.2%, 15/356) (Lancet. 2014; 383:31-39). In particular, FGFR2 amplification was found to be associated with Korean patients with a diffuse histological subtype, and it was confirmed that both the Caucasians (Hazard ratio (HR)=2.37; 95% confidence interval (CI) 1.6-3.5; P=0.0001) and the Koreans (HR=2.33, 95% CI 1.28-4.25, P=0.0129) exhibited remarkably short overall viability.

Meanwhile, through a preclinical result, a strong antitumor efficacy was demonstrated for various FGFR selective and low-molecular inhibitors such as AZD4547, BGJ398, and LY2874455 in a gastric cancer cell line in which FGFR2 was amplified, and consequently, various phase II clinical trials using FGFR selective and low-molecular inhibitors and antibodies are currently being carried out on FGFR2-amplified patients with gastric cancer for a FGFR inhibitory efficacy test. Further, it has been recently reported that in a phase I clinical trial targeting patients with FGFR2b+gastric cancer, FPA144, which is a selective monoclonal antibody against the FGFR2b subtype, showed a response rate of 33% (3 out of 9).

As some factors that are considered to affect the acquisition of resistance to the inhibition of FGFR2, the deletion of mTOR, EGFR, HER, MET and PTEN has been reported through cell line experiments, but the mechanism of acquiring resistance to a FGFR2 inhibitor in a patient has not been elucidated yet. Therefore, in order to obtain the best effect by diagnosing resistance to the anticancer drugs in advance and applying an appropriate treatment method, there is a need for elucidating the mechanism of acquiring resistance to the FGFR2 inhibitor and a biomarker for diagnosing resistance to the FGFR2 inhibitor.

SUMMARY

The present inventors confirmed that a FGFR2-amplified patient with gastric cancer exhibited resistance to a FGFR inhibitor after being treated with the FGFR inhibitor, and as a result of performing RNA sequencing on a tissue in which the resistance is induced, the present inventors found a FGFR2-ACSL5 fusion transcript, thereby completing the present invention based on this finding.

Thus, an object of the present invention is to provide a FGFR2-ACSL5 biomarker capable of diagnosing anticancer drug resistance of gastric cancer and a use thereof.

However, a technical problem to be achieved by the present invention is not limited to the aforementioned problem, and the other problems that are not mentioned may be clearly understood by a person skilled in the art from the following description.

In order to achieve the object of the present invention as described above, the present invention provides a biomarker composition for diagnosing anticancer drug resistance of gastric cancer, including a FGFR2-ACSL5 fusion gene or a protein which the fusion gene encodes.

Further, the present invention provides a composition for diagnosing anticancer drug resistance of gastric cancer, including a preparation which detects an mRNA of a FGFR2-ACSL5 fusion gene or a protein which the fusion gene encodes, and a kit for diagnosing anticancer drug resistance of gastric cancer, including the composition.

As an embodiment of the present invention, the fusion gene may consist of a base sequence of SEQ ID No. 1.

As another embodiment of the present invention, the protein which the fusion gene encodes may consist of an amino acid sequence of SEQ ID No. 2.

As still another embodiment of the present invention, the anticancer drug may be a fibroblast growth factor receptor (FGFR) inhibitor, more specifically, LY2874455, AZD4547, or BGJ398.

As yet another embodiment of the present invention, the preparation which detects the mRNA of the gene may be a sense and antisense primer, or a probe, which binds complementarily to the mRNA of the gene.

As yet another embodiment of the present invention, the preparation which detects the protein may be an antibody which specifically binds to the protein which the fusion gene encodes.

In addition, the present invention provides a method for providing information for diagnosing anticancer drug resistance of gastric cancer, the method including: detecting an mRNA of a FGFR2-ACSL5 fusion gene or a protein which the fusion gene encodes in a biological sample derived from a subject.

As an embodiment of the present invention, the detection of the mRNA may be performed through one or more methods selected from the group consisting of RNA sequencing, polymerase chain reaction (PCR), reverse transcription-polymerase chain reaction (RT-PCR), real-time polymerase chain reaction (Real-Time PCR), the RNase protection assay (RPA), a microarray, and Northern blotting.

As another embodiment of the present invention, the detection of the protein may be performed through one or more methods selected from the group consisting of Western blotting, radioimmunoassay (RIA), radioimmunodiffusion, enzyme-linked immunosorbent assay (ELISA), immunoprecipitation, flow cytometry, immunofluorescence, the Ouchterlony test, the complement fixation assay, and a protein chip.

As still another embodiment of the present invention, the biological sample may be a tumor tissue derived from a patient with gastric cancer.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

The present inventors discovered a biomarker capable of diagnosing anticancer drug resistance of gastric cancer, thereby completing the present invention.

Thus, the present invention provides a biomarker composition for diagnosing anticancer drug resistance of gastric cancer, including a FGFR2-ACSL5 fusion gene or a protein which the fusion gene encodes.

Further, the present invention provides a composition for diagnosing anticancer drug resistance of gastric cancer, including a preparation which detects an mRNA of a FGFR2-ACSL5 fusion gene or a protein which the fusion gene encodes, and a kit for diagnosing anticancer drug resistance of gastric cancer, including the composition.

In the present invention, the "gastric cancer", which is a target disease, is a malignant tumor occurring in the stomach, and includes gastric adenocarcinoma occurring in the gastric mucous epithelium, malignant lymphoma occurring in the submucosal layer, myosarcoma, stromal tumors, and the like, but usually refers to gastric adenocarcinoma. In the present invention, gastric cancer more preferably means gastric cancer in which FGFR2 is amplified.

A FGFR2-ACSL5 fusion gene, which is a biomarker for diagnosing anticancer drug resistance according to the present invention, may consist of a base sequence of SEQ ID No. 1, and the protein which the fusion gene encodes may consist of an amino acid sequence of SEQ ID No. 2.

As used herein, the term "diagnosis" refers to the determination of an actual condition of the disease of a patient in all aspects in a broad sense. The contents of the determination are the disease entity, the etiology, the pathogenesis, the severity, the detailed aspect of a disease, the presence and absence of complications, and the like. In the present invention, the diagnosis includes all of the determination of susceptibility of gastric cancer to an anticancer drug, the determination of whether the present gastric cancer currently has anticancer drug resistance, or the prognosis of anticancer drug-resistant gastric cancer, for example, the determination of cancer responsiveness to anticancer treatment.

In the present invention, the anticancer drug may be a fibroblast growth factor receptor (FGFR) inhibitor, and more preferably may be LY2874455, AZD4547, or BGJ398, which has the following chemical formula structure, respectively, but is not limited thereto as long as the anticancer drug is a drug included in FGFR inhibitors.

[LY2874455]

-continued

[AZD4547]

[BGJ398]

The preparation, which detects the mRNA of the gene, may be a sense and antisense primer, or a probe, which binds complementarily to the mRNA, but is not limited thereto.

As used herein, the term "primer" refers to an oligonucleotide synthesized for the purpose of being used for diagnosis, DNA sequencing, and the like as a short gene sequence which becomes an origin of the DNA synthesis. The primers may be typically synthesized with a length of 15 to 30 base pairs and used, but may vary depending on the purpose of use, and may be modified by methylation and capping or the like through a publicly-known method.

As used herein, the term "probe" refers to a nucleic acid capable of binding specifically to an mRNA having a several or several hundred-base length constructed via enzyme chemical separation and purification or a synthesis process. The probe can identify the presence or absence of an mRNA by labeling a radioactive isotope, an enzyme, a fluorescent material, or the like, and may be designed, modified, and used by a publicly-known method.

The preparation which detects the protein may be an antibody which binds specifically to a protein which a gene encodes, but is not limited thereto.

As used herein, the term "antibody" includes an immunoglobulin molecule having immunological responsiveness to a certain antigen, and includes all of a monoclonal antibody and a polyclonal antibody. Furthermore, the antibody includes a form produced by genetic engineering, such as a chimeric antibody (for example, a humanized murine antibody) and an antibody binding to two different types of antigens (for example, a bispecific antibody).

The kit for diagnosing anticancer drug resistance according to the present invention may consist of one or more other constituent component compositions, solutions or devices suitable for an analysis method.

As another aspect of the present invention, the present invention provides a method for providing information for diagnosing anticancer drug resistance of gastric cancer, the method including: detecting an mRNA of a FGFR2-ACSL5 fusion gene or a protein which the fusion gene encodes in a biological sample derived from a subject.

As used herein, the term "method for providing information for diagnosing anticancer drug resistance" refers to the provision of objective basic information required to diagnose the anticancer drug resistance of gastric cancer as a preliminary step for diagnosis, and a doctor's clinical determination or findings are excluded.

In the present invention, the biological sample may be a gastric tumor tissue, but is not limited as long as the biological sample is a sample derived from a patient with gastric cancer, in which the biomarker for diagnosing anticancer drug resistance according to the present invention is capable of being detected.

The detection of the mRNA may be performed through one or more methods selected from the group consisting of RNA sequencing, polymerase chain reaction (PCR), reverse transcription-polymerase chain reaction (RT-PCR), real-time polymerase chain reaction (Real-Time PCR), the RNase protection assay (RPA), a microarray, and Northern blotting according to a typical method known in the art, and more preferably, may be measured through RNA sequencing, but is not limited thereto.

The detection of the protein may be measured through one or more methods selected from the group consisting of Western blotting, radioimmunoassay (RIA), radioimmunodiffusion, enzyme-linked immunosorbent assay (ELISA), immunoprecipitation, flow cytometry, immunofluorescence, the Ouchterlony test, the complement fixation assay, and a protein chip according to a typical method known in the art, but is not limited thereto.

The present inventors established the FGFR2-ACSL5 fusion gene according to the present invention or a protein thereof as a biomarker capable of diagnosing anticancer drug resistance in gastric cancer through a specific example.

In an example of the present invention, it was confirmed that a patient diagnosed with gastric cancer had a treatment effect while showing susceptibility to LY2874455 which is a FGFR in Borrmann inhibitor, but resistance to the drug is induced along with recurrence 14 months after the treatment (see Example 2).

In another example of the present invention, it was confirmed that FGFR2 was amplified by carrying out IHC and FISH using a gastric cancer biopsy tissue of a patient in which resistance to the drug is induced, but it was confirmed that the degree of amplification of FGFR2 was decreased as compared to that of the tumor tissue prior to the induction of resistance, and based on the results, it was confirmed that as a result of performing RNA sequencing by using a patient-derived tumor tissue, a FGFR2-ACSL5 fusion transcript was expressed in a tissue exhibiting resistance (see Example 3).

In still another example of the present invention, a patient-derived tumor cell line (PDC #1) in which FGFR2 was amplified and the fusion transcript was expressed and a patient-derived tumor cell line(PDC #2) in which FGFR2 was amplified, but the fusion transcript was not expressed were treated with LY2874455 or AZD4547, which is a FGFR inhibitor in order to verify whether the fusion transcript is associated with the acquisition of resistance to the drug. As a result, it was confirmed that only the PDC #1 cell line exhibited resistance, and furthermore, it was confirmed that when the fusion transcript was artificially expressed in PDC #2, resistance was also exhibited.

In addition, as a result of performing the same experiment on a Ba/F3 cell in order to examine the effect of FGFR2-ACSL5 fusion separately from the amplification of FGFR2, it could be seen that resistance to an anticancer drug, which is a FGFR inhibitor, was induced by expression of the FGFR2-ACSL5 fusion transcript (see Example 4).

Through the results of the examples, it was confirmed that the FGFR2-ACSL5 fusion gene or the protein thereof was effective as a biomarker for diagnosing anticancer drug resistance.

Hereinafter, preferable examples are provided to help in understanding the present invention. However, the following examples are provided to more easily understand the present invention and the scope of the present invention is not limited by the following examples.

EXAMPLES

Example 1. Experiment Preparation and Experiment Method 1-1. Subject

The patients participating in the present experiment were enrolled in a molecular screening program, a prospective molecular-profiling study conducted at SMC (Registration ID: NCT02141152), and the experiment was performed after a written informed consent was obtained from all the participants prior to the beginning of the study. Briefly, patients with metastatic solid tumors who were eligible for clinical trial enrollment were eligible to enter the study.

1-2. Analysis of RNA Sequencing, Gene Expression, and Signaling Regulation

RNA sequencing was performed by using a patient sample, and Fastq files obtained through the same were mapped to a human genome reference (hg19) according to the Bowtie method. TopHat was used to generate read counts per gene, and FusionMap was used to discover fusion candidates. An in-house method was developed for inferring the actual read counts supporting the fusion junction and the wild-type sequences of the respective genes. Briefly, the patient gene expression data was corrected with publically available GC data. Gene expression data from the STAD TCGA project (tumor=238, normal=33) was used for normalization purposes. The statistical algorithm COMBAT was used to reduce the impact of platform and batch effects on data analysis. After reducing the batch effect, the patient gene expression levels were standardized by using the mean and standard deviations of normal gastric tissue gene expression values, and individualized pathway alteration scores were obtained according to the IPAS method.

1-3. FGFR2 Fusion Confirmation by Real-Time qRT-PCR

A qRT-PCR assay was performed to validate whether the FGF2 fusion transcript was expressed. More specifically, total RNA was extracted from a biopsy tissue (tumor content>70%) of a resistant tumor and from four formalin-fixed paraffin-embedded tissue sections (4-µm thick) produced through primary tumor biopsies, and then treated with DNase, and the concentration and purity of the extracted RNA were measured by using NanoDrop 8000 (Thermo-Scientific, Wilmington, Del.). Thereafter, a cDNA was synthesized by using a Superscript III First-Strand Synthesis System (Invitrogen, Carlsbad, Calif.) using the RNA as a template. The qRT-PCR was performed by using the TaqMan Gene Expression Master Mix (Part No. 4369016, Applied Biosystems, Foster, City, Calif.), a Custom TaqMan Gene Expression FGFR2-ACSL5 fusion assay (Assay ID AI39SUU; Applied Biosystems), and a fusion-specific primer (5'-CCA GGT AAT GTA AAT GTA CAG CCA CCT GTG CAT TCT GTT TGA CCA TAA GCT TCA TAC ACC TCA TTG GTT GTG AGA GTG AGA ATT CGA TCC AAG TCT TCT ACC AAC TGC-3'; bold, primers; red, probe, SEQ ID No. 3). Further, the expression levels of the GAPDH (Assay ID Hs99999905_m1; Applied Biosystems) gene were measured, and used for calibration.

1-4. FGFR2 Expression Confirmation through FISH and IHC

FISH was carried out by using a ZytoLight SPEC FGFR2/CEN 10 Dual Color Probe (Z-2122-200, Zytovision, Bremerhaven, Germany). 1 µm-thick tumor sections were treated with respective DNA probe sets and cultured overnight at 37° C., and then the hybridization signals were measured in 20 nuclei per sample under a fluorescence microscope. All overlapping nuclei were excluded, only nuclei with a distinct nuclear border were evaluated, and the FGFR2 gene was considered to be amplified when the FGFR2:CEP17 FISH-signal ratio was 2.0 or more.

Meanwhile, IHC was performed to verify whether the FGFR2 protein was expressed in a gastric cancer tissue. More specifically, after the tissue was fixed with formalin, the paraffin-embedded tissue was cut into 4-µm-thick sections, and then the tissue sections were deparaffinized and rehydrated. Next, after antigen retrieval and endogenous peroxidase blocking, the samples were treated with a primary antibody and cultured for 15 minutes. Thereafter, a BOND-MAX autoimmunostainer (Leica Biosystems, Melbourne, Australia) equipped with Bond™ Polymer Refine Detection, DS9800 (Vision Biosystems, Melbourne, Australia) was used according to the manufacturer's protocol.

1-5. Patient-Derived Tumor Cell Culture

Malignant ascites were collected from patients, and the collected ascites (1 to 5 L) were divided and put into 50-mL tubes, centrifuged at 1,500 rpm for 10 minutes, and then washed twice with phosphate-buffered saline (PBS). Thereafter, cell pellets were resuspended in a culture medium, aliquoted into 75-cm$^2$ culture flasks, and then cultured in a Roswell Park Memorial Institute (RPMI) medium containing 10% fetal bovine serum (FBS), 0.5 g/mL hydrocortisone (Sigma Aldrich, St. Louis, Mo.), 5 g/mL insulin (PeproTech, Rocky Hill, N.J.), and 5 ng EGF (PeproTech). After pathological confirmation, confirmed cells were aliquoted at $1\times10^6$ cells/10 mm dishes or 5000 cells/well in 96-well plates and cultured under 37° C. and 5% $CO_2$ conditions for 72 hours. These conditions were also used when immunoblotting and cell proliferation-inhibition results were analyzed, and inhibition of tumor-derived cell line proliferation was confirmed by using the CellTiter-Glo® Reagent (Promega, Madison, Wis.).

1-6. Construction of FGFR2-ACSL5 Constructs

Full-length FGFR2-ACSL5 cDNAs were constructed by splicing partial fragments manufactured from a MegaMan cDNA library (Stratagene, La Jolla, Calif.). Thereafter, the constructed full-length FGFR2-ACSL5 cDNAs were inserted into pcDNA3.1 (Invitrogen) by using the EcoRI/PmeI sites, and sequencing was performed by using an ABI 3730xI DNA analyzer (Thermo Fisher Scientific, Rockford, Ill.) to confirm the open reading frames (ORFs) of the constructs.

1-7. Cell Lines and Transfection

Ba/F3 cells were purchased from the RIKEN BRC CELL BANK (Ibaraki, Japan) and cultured in RPMI 1640 supplemented with 10% fetal bovine serum (FBS) and 1 ng/mL recombinant IL3 (R&D Systems). 2.5 mg of pcDNA3.1/FGFR2 constructs, pcDNA3.1/FGFR2-ACSL5 fusion constructs, or a parental vector pcDNA3.1 were introduced into the cultured $5\times10^6$ cells through electroporation by using a Nucleofector system (Lonza, Basel, Switzerland). The cells into which the constructs were introduced were selected in a medium containing G418 for 2 weeks, and the expression of the full-length fusion transcripts was confirmed by immunoblotting. Meanwhile, in order to verify cell viability, $5\times10^3$ Ba/F3 cells per well were aliquoted repeatedly four times in 96-well plates treated with various concentrations of IL3 or AZD4547, and after 72 hours, the cells were analyzed by using CellTiter-Glo.

1-8. Immunoblot Analysis

Total proteins were extracted from cells by using RIPA buffer (Sigma-Aldrich) containing a protease inhibitor cocktail (Roche) and a phosphatase inhibitor cocktail (Roche), and protein concentrations were measured through a Quick Start Bradford Protein Assay (Bio-Rad, Hercules, Calif.). After 10% sodium dodecyl sulfate (SDS)-polyacrylamide gel electrophoresis (SDS-PAGE) was carried out by using 30 μg of protein in order to perform immunoblotting, the proteins separated by size were transferred to nitocellulose membranes through a transfer process. Next, a blocking process was carried out by treating the membranes with a solution in which 5% nonfat dry milk was diluted in Tris-buffered saline containing 0.1% v/v Tween 20, and after treatment with anti-FGFR2 (Abcam, Cambridge, UK) or anti-beta actin (Sigma Aldrich) antibodies, the membranes were allowed to react overnight at 4° C. Thereafter, the membranes were treated with a horseradish peroxidase-conjugated anti-rabbit or anti-mouse IgG secondary antibody (Vector, Burlingame, Calif.) and allowed to react, and then protein signals were detected by chemiluminescence using an ECL Western Blotting Substrate (Thermo Scientific), and the signals were visualized by using LAS-4000 (Fujifilm, Tokyo, Japan).

Example 2. Case Presentation

Since a 37-year-old female exhibited weight loss and vomiting symptoms, esophagogastroduodenoscopy (EGD) was performed, and as a result, reddish mucosal changes and diffusion accompanied by erythema, debris, and hypertrophy were observed along the entire stomach, and Borrmann type-4 gastric cancer progressed and invaded the duodenum. Therefore, an endoscopic tissue examination was performed, and along with the endoscopic tissue examination, pathological examination of the stomach confirmed signet ring cell carcinoma. Accordingly, a laparoscopic surgery was performed for treatment, but disseminated peritoneal seeding had occurred, so that the surgery was impossible beyond opening and closure, and the tumor was confirmed to be HER2-negative.

The patient underwent eight cycles of oxaliplatin and capecitabine therapy and exhibited a partial response. In the progression, the patient received 12 cycles of 5-fluorouracil and irinotecan (FOLFIRI) every 2 weeks, and exhibited the best partial response. During secondary anticancer chemotherapy, a stent was inserted because the biliary tract was obstructed due to cancerous invasion of the ampulla of Vater. However, immediately after the last cycle of FOLFIRI, a tumorous obstruction developed because of cancer progression, and a stent was inserted to alleviate the obstructive symptom. Further, as tertiary palliative chemotherapy, eight cycles of docetaxel injected on days 1 and 8 were administered every 3 weeks. Thereafter, the patient was enrolled in a phase I clinical trial of LY2874455, a pan-FGFR inhibitor, which inhibits autophosphorylation of FGFR1-4, and it was confirmed that her symptoms were significantly improved immediately after being treated with LY2874455, in a state where ascites completely disappeared.

However, 14 months after the treatment with LY2874455, upper gastrointestinal obstructive symptoms abruptly developed in the patient. The patient consented to transcriptomic profiling for full genomic testing, and for this purpose, upper gastrointestinal stent re-insertion and endoscopic biopsy were carried out followed by total RNA sequencing and targeted amplification at the time of acquiring resistance to LY2874455.

Figure 1A:
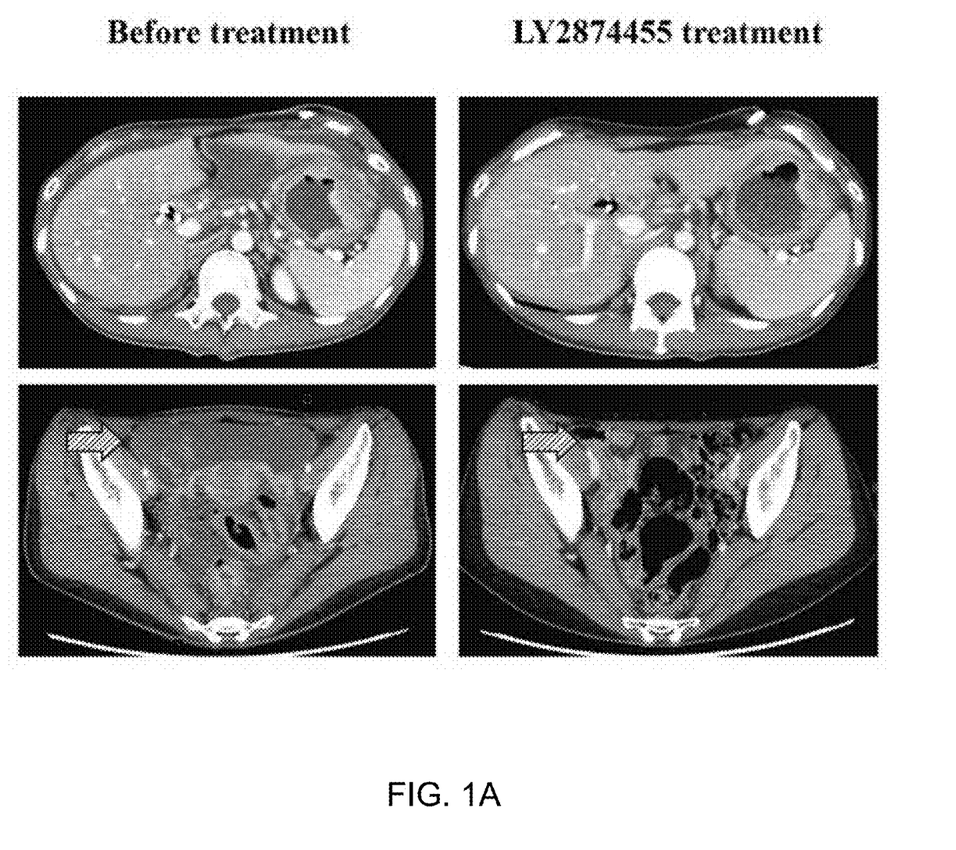
FIG. 1A is a computed tomography (CT) image before and after a patient with gastric cancer is treated with LY2874455.
Figure 1B:
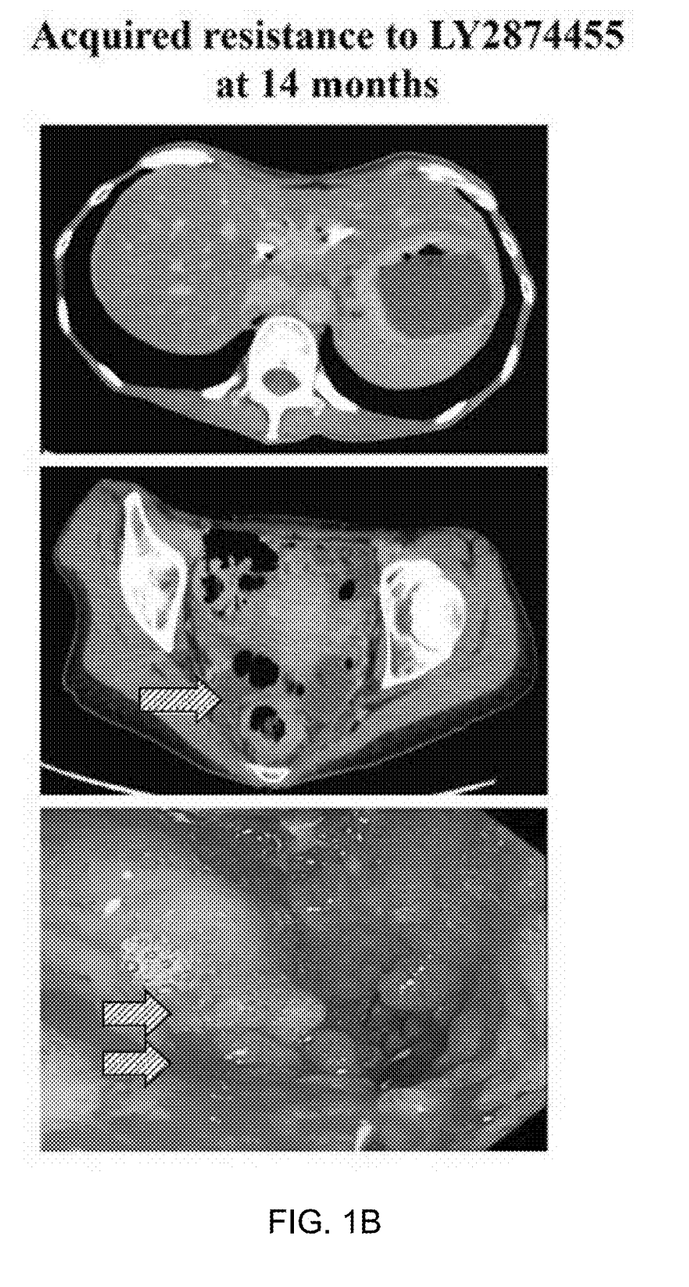
FIG. 1B is an image of a stomach in which seeding of the peritoneum and obstructive stomach tissues occur because resistance to the drug is induced 14 months after treatment with LY2874455.

FIG. 1A illustrates a computed tomography photograph of the patient before and after treatment with LY2874455, and through FIG. 1B, it is possible to confirm a tissue in which resistance to LY2874455 is induced 14 months after the treatment with LY2874455.

Figure 2:
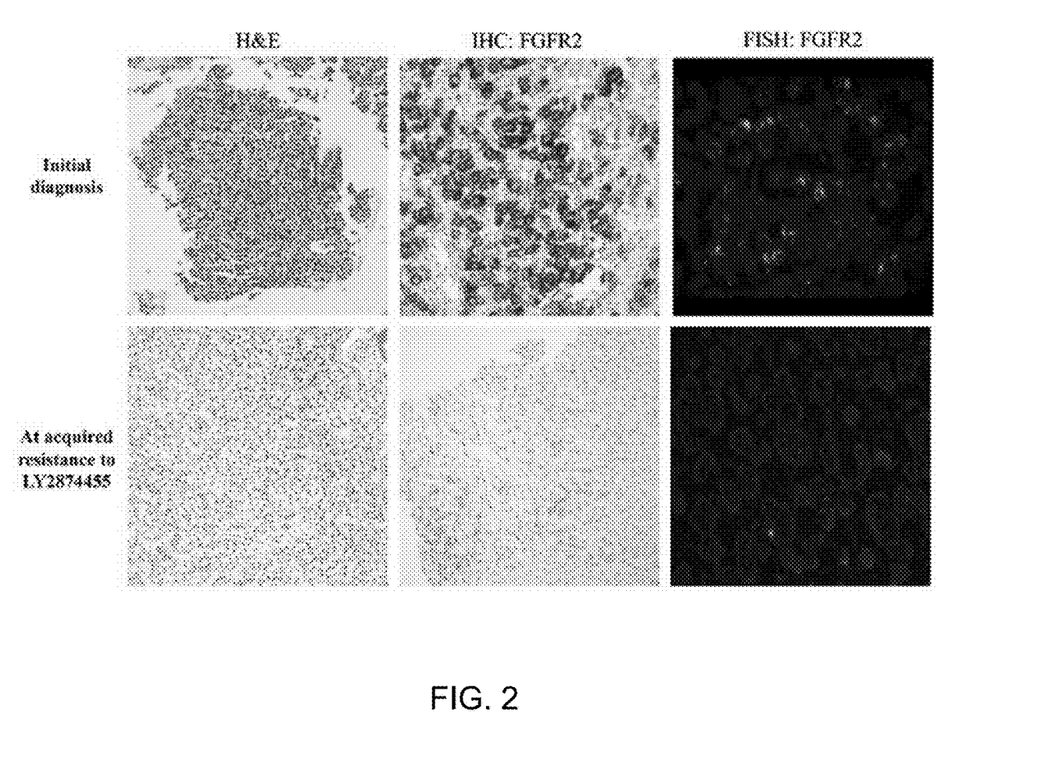
FIG. 2 illustrates the results of carrying out H&E staining and IHC and FISH with respect to FGFR2 on each primary tumor tissue during the diagnosis (initial diagnosis) and after resistance to LY2874455 was induced (at acquired resistance to LY2874455) in a patient with gastric cancer.

Example 3. Confirmation of FGFR2-ACSL5 Fusion Transcript Expression in Tumor Tissue with Acquired Resistance to FGFR Inhibitor In the patient in Example 2, since resistance to LY2874455, a pan-FGFR inhibitor, was induced, an attempt was made to verify whether FGFR2 was expressed in the tumor tissue of the patient. For this purpose, primary gastric cancer tissues were subjected to IHC and FISH at the time of diagnosis and after resistance to the drug was induced. As a result, as illustrated in FIG. 2, it was confirmed that the expression of FGFR2 was amplified in both the membrane and the cytoplasm of the tumor tissue exhibiting resistance to the drug. However, as a result of FISH, the FGFR2 gene copy number was 52.5 in the tumor tissue before the resistance was induced, whereas 2.5 copies were detected in the tissue in which the resistance was induced, so that it was confirmed that FGFR2 was overexpressed in the tumor tissues in the two cases, but the degrees of overexpression were different. In addition, as a result of performing targeted sequencing on the two tissues, no FGFR2 mutations or aberrations other than FGFR2 amplification were detected.

Figure 3:
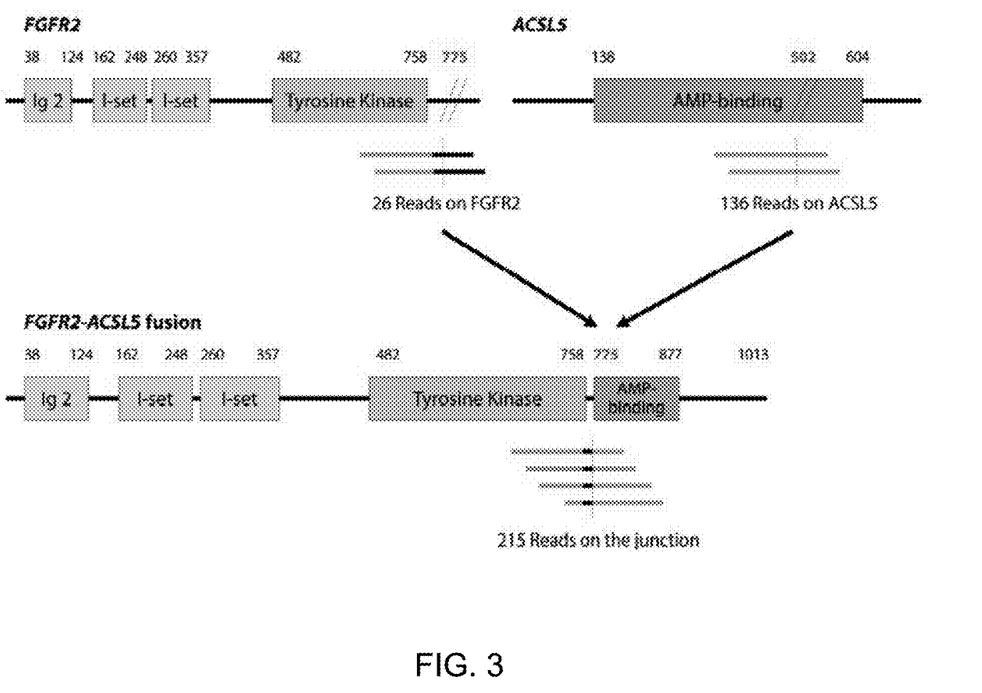
FIG. 3 illustrates a structure of a FGFR2-ACSL5 fusion transcript identified through RNA sequencing.

Based on the results, the present inventors performed RNA transcript sequencing. As a result, it was confirmed that a new FGFR2-ACSL5 fusion protein was present in the tumor tissue exhibiting resistance to the drug. More specifically, as illustrated in FIG. 3, it was confirmed that the fusion protein had a structure in which FGFR2 (NM_022970) was present from the start to the $774^{th}$ amino acid, and connected to the $502^{nd}$ codon of ACSL5 (NM_016234) at the $775^{th}$ amino acid site. Furthermore, it was confirmed that the fusion body included Ig2, I-set, a tyrosine kinase domain of FGFR2, and a truncated AMP-binding domain of ACSL5. Further, an in-house-developed fusion-read validation method showed that 215 read values exactly coincided with the fusion junction, whereas 26 and 136 read values supported the expression of the wild-type FGFR2 and ACSL5 genes, respectively. The larger number of reads showing the gene fusion indicates that the fused form of FGFR2 exhibited elevated expression in the tumor in which resistance is induced. As a result of performing a qRT-PCR assay to verify this, it was confirmed that the level of the FGFR2-ACSL5 fusion transcript was remarkably increased in the tumor in which resistance was induced, but it was confirmed that no fusion transcript was expressed before the treatment and in the baseline tumor tissue.

It was confirmed that the expression of the FGFR2 gene in the patient with gastric cancer was remarkably increased when compared with that in the GC cohort reported in a publically available database (outlier statistic: 3.156). FGFR2 is an up-regulated gene among the receptor tyrosine kinases, indicating that overexpression of the FGFR2 fusion transcript plays an important role in the patient acquiring resistance. It was confirmed that out of the 20 up-regulated pathways in the patient, three pathways (PID ARF6 pathway, BioCarta AKT pathway, and PID PI3KCI pathway) were relevant to the PI3K-AKT-mTOR axis, and notably, phosphorylated FGFR2 can activate the PI3K and AKT pathways through an adapter protein FSR2. According to the ACRG molecular classifications of GC, the patient's tumor was classified as a mesenchymal subtype, but it was not clear whether the up-regulation of these pathways in the tumor resulted from high expression of the FGFR2-ASCL5 fusion product.

Example 4. Confirmation of Correlation Between FGFR2-ACSL5 Fusion and Resistance to FGFR Inhibitor In order to examine effects of the fusion protein on the acquisition of resistance in more detail, the present inventors established a patient-derived tumor cell line (PDC #1) in which FGFR2 was amplified to 2.5 copies and the FGFR2-ACSL5 fusion protein was expressed, and also established a patient-derived tumor cell line (PDC #2) in which the patient had not received chemotherapy treatment, FGFR2 was amplified, but the fused protein was not present.

Figure 4A:
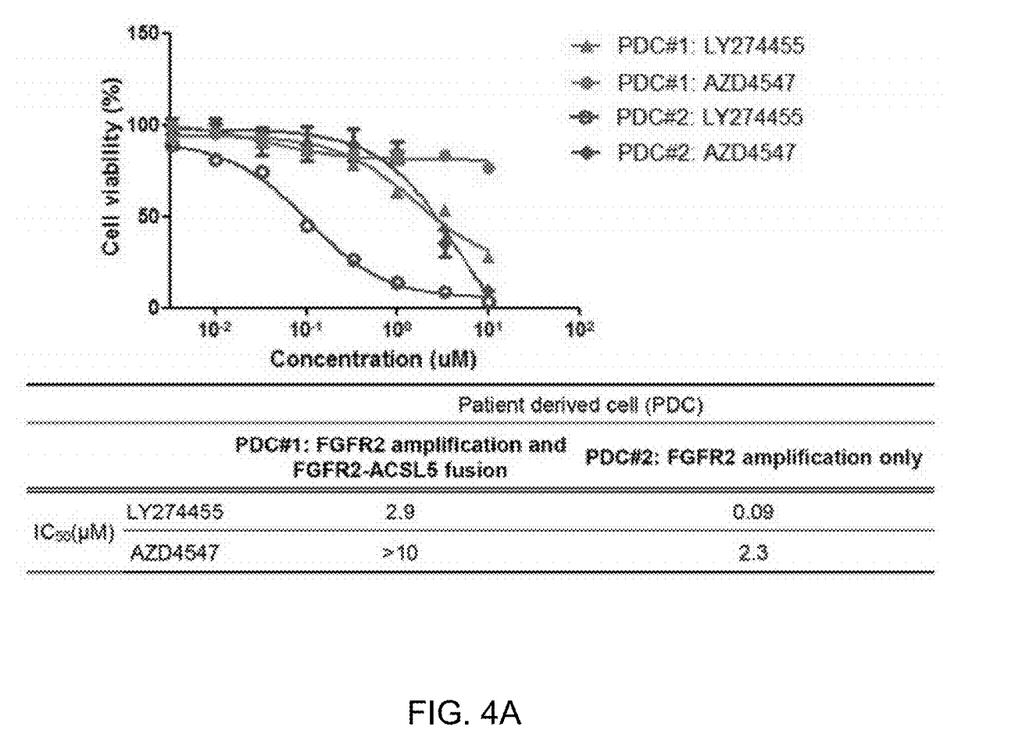
FIG. 4A is a result of analyzing cell viability after each of a patient-derived tumor cell (PDC #1) in which FGFR2 was amplified and a FGFR2-ACSL5 fusion protein was expressed and a patient-derived tumor cell (PDC #2) in which FGFR2 was amplified, but the fusion protein was not expressed was treated with LY2874455 or AZD4547 at various concentrations.
Figure 4B:
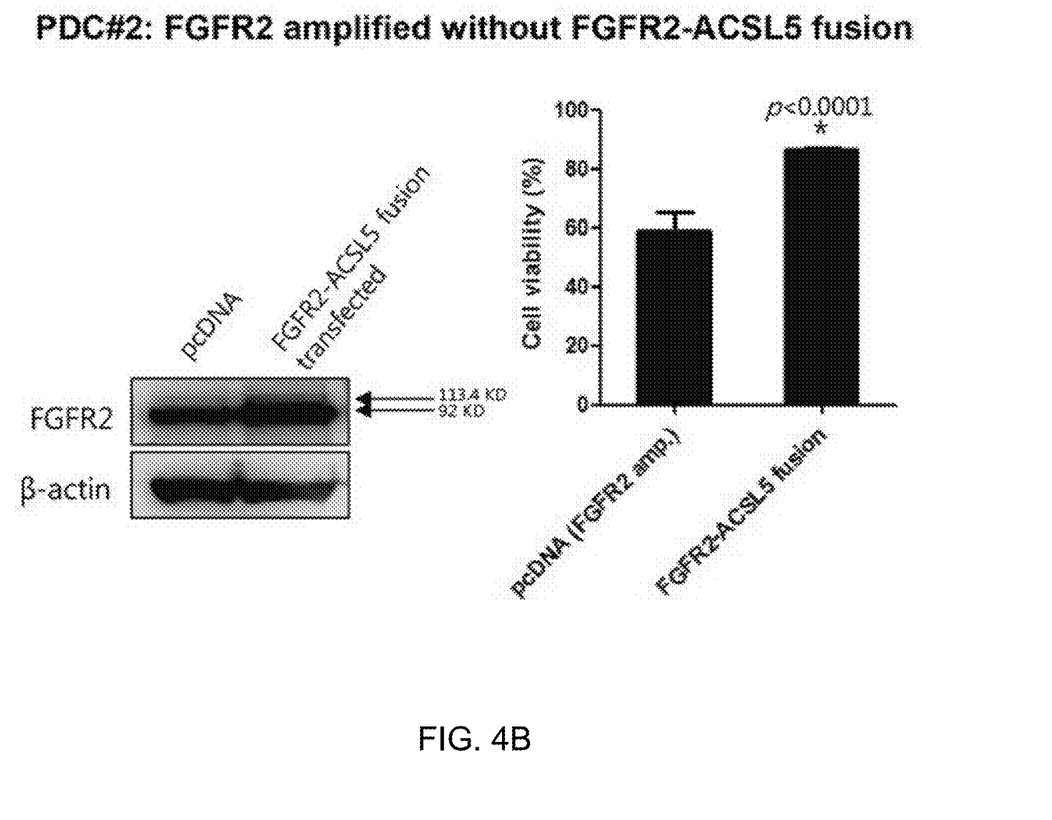
FIG. 4B is a result of artificially expressing the FGFR2-ACSL5 fusion protein in the patient-derived tumor cell (PDC #2) in which FGFR2 was amplified, but the FGFR2-ACSL5 fusion protein was not expressed, and then being treated with AZD4547, and measuring cell viability.

First, after the two cell lines were treated with a FGFR inhibitor LY2874455 or AZD4547, respectively at each concentration, cell viability was measured. As a result, as illustrated in FIG. 4A, it was confirmed that PDC #1 exhibited resistance to both LY2874455 and AZD4547 (2.9 μM and >10 μM of $IC_{50}$, respectively), whereas PDC #2 in which the FGFR2 fusion body was not present and was only amplified did not exhibit resistance. Next, the present inventors transfected PDC #2 with the FGFR2-ACSL5 fusion construct and measured cell viability after treatment with 1 μM of AZD4547. As a result, as illustrated in FIG. 4B, the introduction of the FGFR2-ACSL5 fusion body into a FGFR2-amplified patient-derived tumor cell line (PDC) that was sensitive to FGFR inhibitors resulted in resistance to FGFR inhibitors (cell viability of 86.6% vs 59.2%; 1 μM AZD4547, P<0.0001).

Figure 5A:
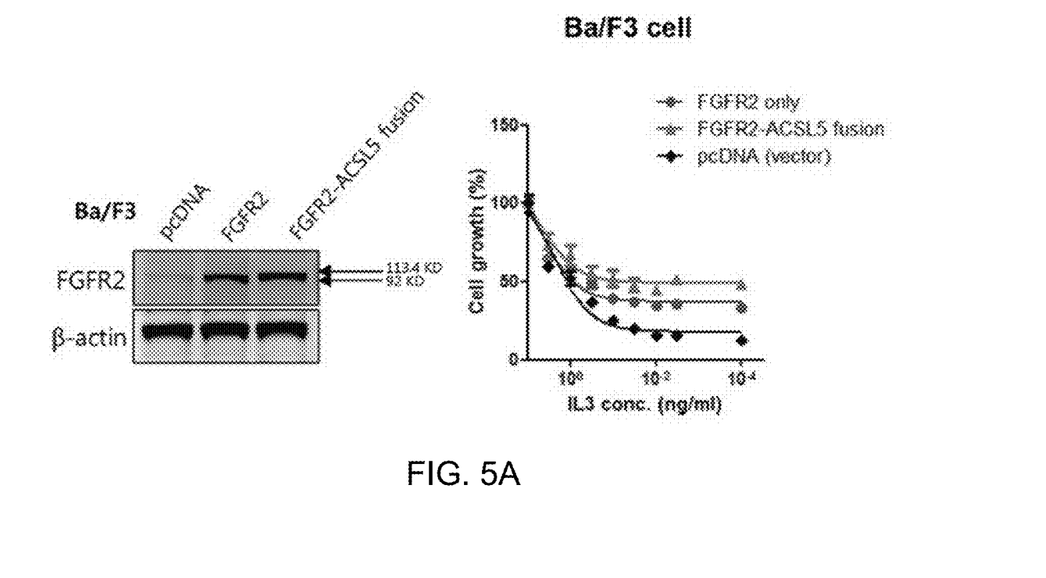
FIG. 5A is a result illustrating the cell proliferation of a control Ba/F3 cell (pcDNA(vector)), a cell in which FGFR2 was expressed alone (FGFR2 only), and a cell in which the FGFR2-ACSL5 fusion protein was expressed according to the concentration of IL3.
Figure 5B:
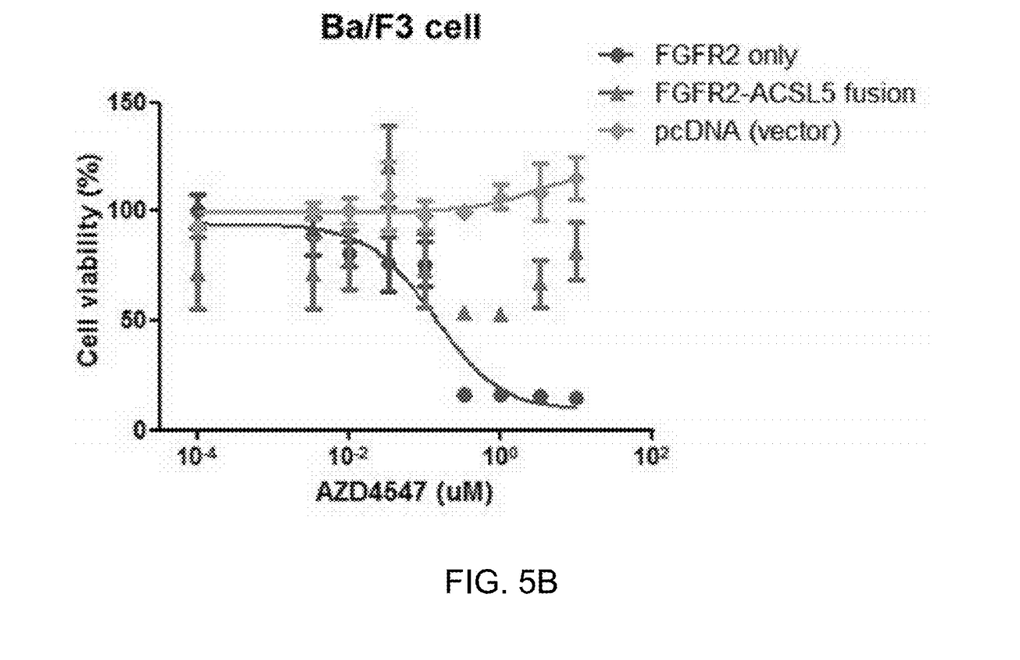
FIG. 5B is a result of measuring cell viability after the respective cells of FIG. 5A were treated with AZD4547.

Furthermore, in order to examine the effects of the FGFR2-ACSL5 fusion separately from FGFR2 amplification, the present inventors transfected Ba/F3 cells with a FGFR2-ACSL5 fusion construct. As a result, as illustrated in FIG. 5A, the murine hematopoietic cell line is IL3-dependent and was independently transformed into IL3 independence by the expression of the FGFR2-ACSL5 fusion protein. Further, as illustrated in FIG. 5B, it was confirmed that isogenic Ba/F3-FGFR2 cells exhibited sensitivity to AZD4547, whereas Ba/F3-FGFR2-ACSL5 cells were induced to be resistant to the drug.

In summary, the FGFR2-ACSL5 fusion was associated with resistance to AZD4547, the FGFR2 inhibitor currently used as a therapeutic agent in patients with FGFR2-amplified tumors.

The inventors of the present invention found that the presence of the FGFR2-ACSL5 fusion transcripts by analyzing the tissues in which FGFR2-amplified patients with gastric cancer showed resistance to FGFR inhibitor treatment, when the fusion transcript was expressed, it was finally confirmed that resistance to FGFR inhibitor was induced. Thus, a biomarker for diagnosing anticancer drug resistance of gastric cancer according to the present invention was discovered. Therefore, by detecting the mRNA of the FGFR2-ACSL5 fusion gene according to the present invention or the protein encoded by the gene in the tissue derived from the patient with gastric cancer, it is possible to diagnose whether the FGFR inhibitor exhibits resistance to the drug in advance, the treatment efficiency can be improved.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method for detecting FGFR2-ACSL5 in a gastric cancer patient with resistance to an anticancer drug, the method comprising:

obtaining a biological sample from a human patient; and detecting whether FGFR2-ACSL5 is present in the biological sample by sequencing the biological sample with probes targeting intronic regions of FGFR2 and ACSL5 and detecting fusion between FGFR2-ACSL5, wherein the anticancer drug is LY2874455 or AZD4547.

2. The method of claim 1, wherein the FGFR2-ACSL5 consists of a nucleotide sequence of SEQ ID No. 1.

3. The method of claim 1, wherein the biological sample is a tumor tissue derived from a patient with gastric cancer.

* * * * *

SEQUENCE LISTING

<160> NUMBER OF SEQ ID NOS: 3

<210> SEQ ID NO 1
<211> LENGTH: 3042
<212> TYPE: DNA
<213> ORGANISM: Artificial Sequence
<220> FEATURE:
<223> OTHER INFORMATION: FGFR2-ACSL5 fusion

<400> SEQUENCE: 1

```
atggtcagct ggggtcgttt catctgcctg gtcgtggtca ccatggcaac cttgtccctg      60
gcccggccct ccttcagttt agttgaggat accacattag agccagaaga gccaccaacc     120
aaataccaaa tctctcaacc agaagtgtac gtggctcgc caggggagtc gctagaggtg     180
cgctgcctgt tgaaagatgc cgccgtgatc agttggacta aggatggggt gcacttgggg     240
cccaacaata ggacagtgct tattggggag tacttgcaga taaagggcgc cacgcctaga     300
gactccggcc tctatgcttg tactgccagt aggactgtag acagtgaaac ttggtacttc     360
atggtgaatg tcacagatgc catctcatcc ggagatgatg aggatgacac cgatggtgcg     420
gaagattttg tcagtgagaa cagtaacaac aagagagcac catactggac caacacagaa     480
aagatggaaa agcggctcca tgctgtgcct gcggccaaca ctgtcaagtt tcgctgccca     540 gccggggga acccaatgcc aaccatgcgg tggctgaaaa acgggaagga gtttaagcag     600
```

```
gagcatcgca ttggaggcta caaggtacga aaccagcact ggagcctcat tatggaaagt    660
gtggtcccat ctgacaaggg aaattatacc tgtgtagtgg agaatgaata cgggtccatc    720
aatcacacgt accacctgga tgttgtggag cgatcgcctc accggcccat cctccaagcc    780
ggactgccgg caaatgcctc cacagtggtc ggaggagacg tagagtttgt ctgcaaggtt    840
tacagtgatg cccagcccca catccagtgg atcaagcacg tggaaaagaa cggcagtaaa    900
tacgggcccg acgggctgcc ctacctcaag gttctcaagc actcggggat aaatagttcc    960
aatgcagaag tgctggctct gttcaatgtg accgaggcgg atgctgggga atatatatgt   1020
aaggtctcca attatatagg gcaggccaac cagtctgcct ggctcactgt cctgccaaaa   1080
cagcaagcgc ctggaagaga aaaggagatt acagcttccc cagactacct ggagatagcc   1140
atttactgca taggggtctt cttaatcgcc tgtatggtgg taacagtcat cctgtgccga   1200
atgaagaaca cgaccaagaa gccagacttc agcagccagc cggctgtgca caagctgacc   1260
aaacgtatcc ccctgcggag acaggtaaca gtttcggctg agtccagctc ctccatgaac   1320
tccaacaccc cgctggtgag gataacaaca cgcctctctt caacggcaga caccccatg   1380 ctggcagggg tctccgagta tgaacttcca gaggacccaa aatgggagtt tccaagagat   1440
aagctgacac tgggcaagcc cctgggagaa ggttgctttg gcaagtggt catggcggaa   1500 gcagtgggaa ttgacaaaga caagcccaag gaggcggtca ccgtggccgt gaagatgttg   1560
aaagatgatg ccacagagaa agacctttct gatctggtgt cagagatgga gatgatgaag   1620
atgattggga aacacaagaa tatcataaat cttcttggag cctgcacaca ggatgggcct   1680
ctctatgtca tagttgagta tgcctctaaa ggcaacctcc gagaatacct ccgagcccgg   1740
aggccacccg ggatggagta ctcctatgac attaaccgtg ttcctgagga gcagatgacc   1800
ttcaaggact tggtgtcatg cacctaccag ctggccagag gcatggagta cttggcttcc   1860
caaaaatgta ttcatcgaga tttagcagcc agaaatgttt tggtaacaga aaacaatgtg   1920
atgaaaatag cagactttgg actcgccaga gatatcaaca atatagacta ttacaaaaag   1980
accaccaatg gcggcttcc agtcaagtgg atggctccag aagccctgtt tgatagagta   2040
tacactcatc agagtgatgt ctggtccttc ggggtgttaa tgtgggagat cttcactta   2100 gggggctcgc cctacccagg gattcccgtg gaggaacttt ttaagctgct gaaggaagga   2160
cacagaatgg ataagccagc caactgcacc aacgaactgt acatgatgat gagggactgt   2220
tggcatgcag tgccctccca gagaccaacg ttcaagcagt tggtagaaga cttggatcga   2280
attctcactc tcacaaccaa tgaggaatac ttggacctca gccaaacaga atgcacaggt   2340
ggctgtacat ttacattacc tgggactgg acatcaggtc acgttggggt gccctggct   2400 tgcaattacg tgaagctgga agatgtggct gacatgaact actttacagt gaataatgaa   2460
ggagaggtct gcatcaaggg tacaaacgtg ttcaaggat acctgaagga ccctgagaag   2520
acacaggaag ccctggacag tgatggctgg cttcacacag agacattgg tcgctggctc   2580 ccgaatggaa ctctgaagat catcgaccgt aaaaagaaca tttcaagct ggcccaagga   2640 gaatacattg caccagagaa gatagaaaat atctacaaca ggagtcaacc agtgttacaa   2700 attttttgtac acggggagag cttacggtca tccttagtag agtggtggt tcctgacaca   2760 gatgtacttc cctcatttgc agccaagctt ggggtgaagg gctcctttga ggaactgtgc   2820
caaaaccaag ttgtaaggga agccatttta gaagacttgc agaaaattgg gaaagaaagt   2880
ggccttaaaa ctttttgaaca ggtcaaagcc attttttcttc atccagagcc attttccatt   2940
```

```
gaaaatgggc tcttgacacc aacattgaaa gcaaagcgag gagagctttc caaatacttt      3000
cggacccaaa ttgacagcct gtatgagcac atccaggatt ag                        3042
```

```
<210> SEQ ID NO 2
<211> LENGTH: 1013
<212> TYPE: PRT
<213> ORGANISM: Artificial Sequence
<220> FEATURE:
<223> OTHER INFORMATION: FGFR2-ACSL5 fusion

<400> SEQUENCE: 2
```

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350
```

```
Ala Trp Leu Thr Val Leu Pro Lys Gln Gln Ala Pro Gly Arg Glu Lys
            355                 360                 365

Glu Ile Thr Ala Ser Pro Asp Tyr Leu Glu Ile Ala Ile Tyr Cys Ile
        370                 375                 380

Gly Val Phe Leu Ile Ala Cys Met Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
                420                 425                 430

Ala Glu Ser Ser Ser Met Asn Ser Asn Thr Pro Leu Val Arg Ile
            435                 440                 445

Thr Thr Arg Leu Ser Ser Thr Ala Asp Thr Pro Met Leu Ala Gly Val
        450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
            500                 505                 510

Val Thr Val Ala Val Lys Met Leu Lys Asp Asp Ala Thr Glu Lys Asp
        515                 520                 525

Leu Ser Asp Leu Val Ser Glu Met Glu Met Met Lys Met Ile Gly Lys
530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
        595                 600                 605

Tyr Gln Leu Ala Arg Gly Met Glu Tyr Leu Ala Ser Gln Lys Cys Ile
            610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765
```

```
Glu Tyr Leu Asp Leu Ser Gln Thr Glu Cys Thr Gly Gly Cys Thr Phe
    770             775                 780
Thr Leu Pro Gly Asp Trp Thr Ser Gly His Val Gly Val Pro Leu Ala
785             790                 795                 800
Cys Asn Tyr Val Lys Leu Glu Asp Val Ala Asp Met Asn Tyr Phe Thr
            805                 810                 815
Val Asn Asn Glu Gly Glu Val Cys Ile Lys Gly Thr Asn Val Phe Lys
            820                 825                 830
Gly Tyr Leu Lys Asp Pro Glu Lys Thr Gln Glu Ala Leu Asp Ser Asp
            835                 840                 845
Gly Trp Leu His Thr Gly Asp Ile Gly Arg Trp Leu Pro Asn Gly Thr
850             855                 860
Leu Lys Ile Ile Asp Arg Lys Lys Asn Ile Phe Lys Leu Ala Gln Gly
865             870                 875                 880
Glu Tyr Ile Ala Pro Glu Lys Ile Glu Asn Ile Tyr Asn Arg Ser Gln
            885                 890                 895
Pro Val Leu Gln Ile Phe Val His Gly Glu Ser Leu Arg Ser Ser Leu
            900                 905                 910
Val Gly Val Val Pro Asp Thr Asp Val Leu Pro Ser Phe Ala Ala
            915                 920                 925
Lys Leu Gly Val Lys Gly Ser Phe Glu Glu Leu Cys Gln Asn Gln Val
930                 935                 940
Val Arg Glu Ala Ile Leu Glu Asp Leu Gln Lys Ile Gly Lys Glu Ser
945             950                 955                 960
Gly Leu Lys Thr Phe Glu Gln Val Lys Ala Ile Phe Leu His Pro Glu
                965                 970                 975
Pro Phe Ser Ile Glu Asn Gly Leu Leu Thr Pro Thr Leu Lys Ala Lys
            980                 985                 990
Arg Gly Glu Leu Ser Lys Tyr Phe Arg Thr Gln Ile Asp Ser Leu Tyr
            995                 1000                1005
Glu His Ile Gln Asp
        1010

<210> SEQ ID NO 3
<211> LENGTH: 108
<212> TYPE: DNA
<213> ORGANISM: Artificial Sequence
<220> FEATURE:
<223> OTHER INFORMATION: fusion-specific primer

<400> SEQUENCE: 3
ccaggtaatg taaatgtaca gccacctgtg cattctgttt gaccataagc ttcatacacc      60
tcattggttg tgagagtgag aattcgatcc aagtcttcta ccaactgc                 108
```